(12) United States Patent
Stoehr

(10) Patent No.: US 7,427,601 B2
(45) Date of Patent: Sep. 23, 2008

(54) METHOD FOR TREATING TREMOR

(75) Inventor: Thomas Stoehr, Monheim (DE)

(73) Assignee: Schwarz Pharma AG, Monheim (DE)

( * ) Notice: Subject to any disclaimer, the term of this patent is extended or adjusted under 35 U.S.C. 154(b) by 0 days.

(21) Appl. No.: 11/149,181

(22) Filed: Jun. 10, 2005

(65) Prior Publication Data

US 2005/0288234 A1    Dec. 29, 2005

Related U.S. Application Data

(60) Provisional application No. 60/582,084, filed on Jun. 24, 2004.

(51) Int. Cl.
*A61K 38/00* (2006.01)
(52) U.S. Cl. .......................... 514/19; 530/300; 600/595
(58) Field of Classification Search ........................ None
See application file for complete search history.

(56) References Cited

U.S. PATENT DOCUMENTS

| | | | |
|---|---|---|---|
| 5,378,729 A | 1/1995 | Kohn et al. | |
| 5,773,475 A * | 6/1998 | Kohn | 514/616 |
| 6,197,764 B1 | 3/2001 | Bradley et al. | 514/218 |
| 6,277,825 B1 | 8/2001 | Olivera et al. | 514/13 |
| 6,884,910 B2 * | 4/2005 | Harris | 562/553 |
| 2003/0180332 A1 * | 9/2003 | Rimpler et al. | 424/400 |
| 2005/0227961 A1 | 10/2005 | Speicher | 514/211.13 |
| 2005/0261204 A1 | 11/2005 | Stoehr | 514/19 |
| 2005/0277596 A1 | 12/2005 | Stoehr | 514/19 |

FOREIGN PATENT DOCUMENTS

| | | |
|---|---|---|
| EP | 1 486 205 | 12/2004 |
| EP | 1 486 206 | 12/2004 |
| WO | WO 00/51586 | 9/2000 |
| WO | WO 02/15922 | 2/2002 |
| WO | WO 02/42256 | 5/2002 |
| WO | WO 02/74297 | 9/2002 |
| WO | WO 02/74784 | 9/2002 |
| WO | WO 2004/046178 A2 | 6/2004 |

OTHER PUBLICATIONS

"Retrieved from" http://www.wrongdiagnosis.com/sym/tremor_symptoms.htm) 2003, [retrived on Aug. 23, 2006].*
"Retrieved from", www.jstage.jst.go.jp/article/yakushi/121/4/121_259/_article/-char/en, [retriecved on Aug. 22, 2006], Suemaru, et al., Yakugaku Zasshi, 2001, vol. 121, 259-264, (abstract only).*
"Retrieved from" http://www.healthatoz.com/healthatoz/Atoz/dc/caz/neur/park/park_gen_prev.jsp Jun. 2006, [retrieved on Aug. 24, 2006].*
"Retrieved from" http://www.ninds.nih.gov/disorders/tremor/tremor.htm Jul. 2006, [retrieved on Aug. 22, 2006].*
[Retrived from website] 'http://www.answers.com/topic/prevent', 4 pages [retrieved on Jan. 22, 2007].*
Suemaru, et al., Yakugaku Zasshi, 2001, vol. 121, 21 pages [Translation].*
Bialer, et al., 2002, Epilepsy Research 51, 31-71.*
Hovinga, IDrugs 6(5):479-485, 2003.
Arroyo (2003) "Safety of SPM 927 in subjects with epilepsy and neuropathic pain" Poster presented at AES Scientific Exhibit, Dec. 5-10, 2003.
Baisara (1982) Ind. J. Physiol. Pharmacol. 26(3): 184-195.
Beyreuthe et al. (2007) CNS Drug Rev. 13(1):21-42.
Brodie (1996) Can. J. Neurol. Sci. 23(Suppl. 2):S6-S9.
Daniels et al. (2005) "Long-term safety and efficacy of lacosamide as adjunctive therapy in subjects with partial seizures: 96-week follow-up" Poster presented at AES Scientific Exhibit, Dec. 2-5, 2005.
Domino & Sheng (1993) J. Pharmacol. Exp. Ther. 264(1):221-225.
Doty et al. (2004) "Update on the clinical development of SPM 927 (formerly harkoseride)" Presented at EILAT VII, May 2004.
Duncan & Kohn (2005) Epilepsy Res. 67:81-87.
Fleminger (1999) Therapeutics 2(4):118.
Hidvegi et al. (2006) "Lacosamide in subjects with painful distal diabetic neuropathy: results of multi-center, open-label, follow-on trial" Poster presented at American Pain Society, May 3-6, 2006.
Kenney et al. (2006) http://www.ampainsoc.org/db2/abstract/view?poster_id=2773#774.
Mar. (1985) Advanced Organic Chemistry, New York: Wiley, pp. 16-18.
Porter et al. (1984) Cleveland Clinic Quarterly 51(2):293-305.
Rauck et al. (2007) Clin. J. Pain 23(2):150-158.
Sachdeo et al. (2003) "An open-label, maximum tolerated dose trial to evaluate oral SPM 927 as adjunctive therapy in patients with partial seizures" Poster presented at 55th Annual Meeting, American Academy of Neutology, Mar. 2003.
Shaibani et al. (2005) "An open-label follow-on trial to assess the long-term safety and efficacy of oral lacosamide in subjects with diabetic neuropathy" Poster presented at World Congress on Pain, Aug. 21-26, 2005.
Sommerville (2003) "Schwarz Pharma's Neurology Pipeline" http://www.schwarzpharma.com/_uploads/assets/1369_4_neurology_KNS_190203.pdf.
Stables & Kupferberg (1997) in Avanzani et al. "Molecular and Cellular Targets for Antiepileptic Drugs", chap. 16, pp. 191-198; London: Libbey.
Wymer et al. (2005) "A multi-center, randomized double-blind, placebo-controlled trial to assess the efficacy and safety of lacosamide in subjects with painful distal diabetic neuropathy," 8th Int. Conf. on Mechanisms and Treatment of Neuropathic Pain, San Francisco, Nov. 3-5, 2005.

* cited by examiner

*Primary Examiner*—Andrew D. Kosar
*Assistant Examiner*—Satyanarayana Gudibande
(74) *Attorney, Agent, or Firm*—Harness, Dickey & Pierce, P.L.C.

(57) ABSTRACT

The present invention is directed to the use of a class of peptide compounds for treating essential tremor and other tremor syndromes.

14 Claims, No Drawings

METHOD FOR TREATING TREMOR

CROSS REFERENCE TO RELATED APPLICATION

This application claims the benefit of U.S. Provisional Ser. No. 60/582,084, filed Jun. 24, 2004.

The present invention is directed to the use of a class of peptide compounds for treating essential tremor and other tremor syndromes.

Certain peptides are known to exhibit central nervous system (CNS) activity and are useful in the treatment of epilepsy and other CNS disorders. These peptides which are described in the U.S. Pat. No. 5,378,729 have the Formula (Ia):

$$R-NH-\underset{\underset{O}{\|}}{\overset{\overset{R_2}{|}}{C}}-\underset{\underset{R_3}{|}}{C}NH\underset{n}{\rbrack}\underset{\underset{O}{\|}}{C}-R_1 \qquad \text{Formula (Ia)}$$

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group or electron donating group;

$R_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group; and $R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z-Y wherein $R_2$ and $R_3$ may be unsubstituted or substituted with at least one electron withdrawing group or electron donating group;

Z is O, S, $S(O)_a$, $NR_4$, $PR_4$ or a chemical bond;

Y is hydrogen, lower alkyl, aryl, aryl lower alkyl, lower alkenyl, lower alkynyl, halo, heterocyclic, heterocyclic lower alkyl, and Y may be unsubstituted or substituted with an electron donating group or an electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$ or $PR_4SR_7$, $NR_4PR_4R_6$ or $PR_4NR_5R_7$, $$\underset{\underset{O}{\|}}{NR_4C}-R_5, \quad \underset{\underset{O}{\|}}{SCR_5}, \quad \underset{\underset{O}{\|}}{NR_4C}-OR_5, \quad \underset{\underset{O}{\|}}{SC}-OR_5;$$

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group; and $R_7$ is $R_6$ or $COOR_8$ or $COR_8$;

$R_8$ is hydrogen or lower alkyl, or aryl lower alkyl, and the aryl or alkyl group may be unsubstituted or substituted with an electron withdrawing group or an electron donating group; and n is 1-4; and a is 1-3.

U.S. Pat. No. 5,773,475 also discloses additional compounds useful for treating CNS disorders. These compounds are N-benzyl-2-amino-3-methoxy-propionamide having the Formula (IIa):

$$Ar-CH_2-\underset{\underset{O}{\|}}{\overset{\overset{H}{|}}{N}}-\underset{\underset{CH_2}{|}}{\overset{\overset{H}{|}}{C}}-\underset{}{\overset{\overset{H}{|}}{N}}-\underset{\underset{O}{\|}}{C}-R_1 \qquad \text{Formula (IIa)}$$
$$\phantom{Ar-CH_2-N-C-}\underset{R_3}{|}$$

wherein

Ar is aryl which is unsubstituted or substituted with halo; $R_3$ is lower alkoxy; and $R_1$ is methyl.

The U.S. Pat. No. 5,378,729 and U.S. Pat. No. 5,773,475 are hereby incorporated by reference. However, neither of these patents describes the use of these compounds for treating essential tremor and other tremor syndromes.

WO 02/074297 relates to the use of a compound according to Formula (IIa) wherein Ar is phenyl which may be substituted by at least one halo, $R_3$ is lower alkoxy containing 1-3 carbon atoms and $R_1$ is methyl for the preparation of pharmaceutical compositions useful for the treatment of allodynia related to peripheral neuropathic pain.

WO 02/074784 relates to the use of a compound having Formula (Ia) or/and Formula (IIa) showing antinociceptive properties for treating different types and symptoms of acute and chronic pain, especially non neuropathic inflammatory pain, e.g. rheumatoid arthritic pain or/and secondary inflammatory osteo-arthritic pain.

Tremor refers to rhythmic shaking of a body part and is defined as an involuntary, rhythmic oscillatory movement of a part or parts of the body, resulting from alternating or irregularly synchronous contractions of antagonist muscles. Tremor is the most common form of involuntary movement. Almost all individuals have experienced tremor at some point in their lives; however, only a small fraction of those with tremor seek medical attention. Tremors may result from normal (physiologic) or pathological processes and may be characterized by their etiology or phenomenology (i.e., activation state, frequency, amplitude, waveform). With the exception of those affecting the facial region, tremors are frequently defined or characterized by the joint around which the body part moves.

Descriptive terms used to describe the clinical phenomenology of tremor include rest tremors and action tremors (see Table 1). Rest tremor occurs when muscle is not voluntarily activated, whereas action tremor is present with voluntary contraction of muscle. Subtypes include postural, kinetic, and isometric tremor. Postural tremor is present while voluntarily maintaining a position against gravity. Kinetic tremor may occur during any form of voluntary movement. Intention or terminal tremor refers to exacerbation of kinetic tremor toward the end of a goal-directed movement.

TABLE 1

Classification of Tremor by Clinical Phenomenology

| | |
|---|---|
| Rest tremor | Present when skeletal muscles are not voluntarily activated and the relevant body part is fully supported against gravity. Associated with Parkinson's Disease, secondary parkinsonism, hereditary chin quivering, and severe essential tremor (ET). Often suppressed with voluntary muscle contraction. |
| Action tremor | Occurs upon any voluntary muscle contraction and may include any combination of postural, kinetic, task- or position-specific, or isometric tremor. |
| Postural tremor | An action tremor that is present while voluntarily maintaining a position against gravity. Associated with ET, primary orthostatic tremor, physiologic and enhanced physiological tremors, drug-induced and toxic tremors, neuropathic tremor, cerebellar head tremor (titubation), and dystonic tremor. |
| Kinetic tremor | An action tremor that occurs with any form of voluntary movement including visually- or nonvisually-guided actions, such as speaking, pouring water into a cup, or finger-to-nose testing. Associated with ET, classic cerebellar tremor (e.g., seen in multiple sclerosis, infarction), dystonic tremor, drug-induced or toxic tremors, and midbrain lesions. Includes dynamic or terminal tremor, which occurs with target-directed movements, and simple kinetic tremor, which is present with nontarget-directed actions. |
| Task- or position-specific tremor | A kinetic tremor that occurs during performance of highly specialized, complex movements, such as writing, speaking, or smiling. Primary writing tremor and isolated voice tremor are included. |
| Isometric tremor | A kinetic tremor present during voluntary muscle contraction against a rigid stationary object, such as making a fist or flexing the wrist against a horizontal, flat surface. |

Tremor may be further delineated by anatomic distribution (e.g., the head, including the chin, face, tongue, or palate, or the upper or lower extremities); frequency; and coexistent neurologic conditions, use of tremorogenic medications, or other causative states.

There are more than 20 kinds of tremor. Essential tremor (ET) is the most common.

ET is a common neurologic movement disorder. Estimates suggest that ET may be as much as 10 to 20 times as prevalent as Parkinson's disease (PD), affecting from 5 million up to as many as 10 million people in the United States. In the past, the condition was often referred to as "benign essential tremor." However, many experts consider use of the term "benign" unfortunate, since it may inappropriately minimize the impact of ET on disability, handicap, and quality of life.

Since practical classifications of tremor that are based upon etiologic or pathophysiologic factors are not available, tremor research typically relies on clinical classifications. The clinical classification of tremor may be based upon:

Clinical phenomenology
Anatomic or topographic distribution
Activities that activate tremor
Relative tremor frequency measured in cycles per second
Medical and drug history and clinical evaluation (i.e., to detect concomitant neurologic conditions, drug-induced or toxic tremors, etc.)

The definition of the clinical classification of ET is an ongoing, evolutionary process. Several classification schema have been proposed including the Consensus Statement of the Movement Disorder Society (MDS) on Tremor in 1997 (see Table 2).

TABLE 2

Consensus Statement of the Movement Disorder Society

| | |
|---|---|
| Classic ET: Inclusion Criteria | 1. Bilateral, largely postural or kinetic tremor involving the hands and forearms |
| | 2. Tremor is persistent and visible |
| Classic ET: Exclusion Criteria | 1. Other abnormal neurologic signs (particularly dystonia) |
| | 2. Presence of known causes of enhanced physiologic tremor |
| | 3. Historical or clinical evidence of psychogenic tremor |
| | 4. Convincing evidence of sudden onset or stepwise deterioration |
| | 5. Primary orthostatic tremor |
| | 6. Isolated voice tremor |
| | 7. Isolated position- or task-specific tremor |
| | 8. Isolated tongue or chin tremor |
| | 9. Isolated leg tremor |

ET must also be differentiated from other specific tremor types. These include enhanced physiologic, drug-induced, toxic, dystonic, or parkinsonian tremors. For example, isolated head tremor in ET must be excluded from head tremor seen in up to 40% of patients with cervical dystonia. In ET patients, head tremor is characterized by rhythmic, regular oscillations, whereas that associated with cervical dystonia tends to be irregular, occurs with tilting of the head or chin, and varies in intensity with position changes. ET and parkinsonian tremor may be characterized by postural, kinetic, and resting tremor components. However, traditionally, PD is primarily characterized by rest tremor that dampens with action, whereas ET is generally a postural/kinetic tremor with dampening upon rest. In addition, PD almost never involves tremor of the head or voice yet may involve the chin and perioral structures.

In addition to classic ET, the MDS consensus criteria describe several additional syndromes based upon clinical observations of specific tremor elements. Important in the differential diagnosis of ET, these syndromic tremor classifications include the following:

Physiologic tremor. A normal phenomenon, physiologic tremor occurs in all contracting muscle groups. Ranging in frequency from 8 to 12 Hz, it is subtly detectable on electromyography (EMG). Although seldom visible to the naked eye, physiologic tremor may often be detected when the fingers are firmly outstretched with a piece of paper placed over the hands.

Enhanced physiologic tremor or an intensification of physiologic tremor to detectable levels. Physiologic tremor may be enhanced under conditions of stress, anxiety, fatigue, exercise, cold, hunger, stimulant use, alcohol withdrawal, or metabolic disturbances, such as hypoglycemia or hyperthyroidism.

Undetermined tremor syndrome. Patients with indeterminate tremor syndrome fulfill the criteria for classic ET yet have additional neurologic signs that are insufficient for diagnosis of another neurologic disorder.

Primary orthostatic tremor, a postural tremor of lower limb, trunk, and, possibly, upper limb muscles during stance yet absent when sitting or reclining. In most patients, orthostatic tremor is suppressed upon walking. As seen on EMG, orthostatic tremor is characterized by high frequency, 13 to 18 Hz entrainment of synchronous motor unit activity of contralateral and ipsilateral muscles, primarily of the lower limbs.

Dystonic tremor. Although consensus has not been reached concerning the definition of dystonic tremor syndrome, authors of the MDS consensus criteria have proposed a number of definitions within this general category. For example, "dystonic tremor" refers to primarily postural and kinetic tremor occurring in a body part affected by dystonia.

Task- and position-specific tremors. These tremors occur upon performance of specific, highly specialized motor activities. They include primary writing tremor, defined as tremor occurring solely or primarily while writing yet not with other hand activities; occupational tremors, such as specific tremors affecting athletes or musicians; or isolated voice tremors.

Parkinsonian tremor syndromes, i.e., the presence of pathologic tremor in patients with PD. PD is a slowly progressive, degenerative disorder of the central nervous system (CNS) that may be characterized by tremor (primarily resting tremor), rigidity, and bradykinesia or slowness and poverty of movement. Whereas rest tremor is a diagnostic criterion for PD, other forms of tremor may also be present.

Cerebellar tremor syndromes, described as pure or primary intention tremors with a frequency predominantly less than 5 Hz, possibly in association with postural (but not resting) tremor. The terms "cerebellar" and "intention" tremor are often used interchangeably.

Holmes tremor. Traditionally known as rubral or midbrain tremor, so-called Holmes tremor is defined as a symptomatic rest, intention, and possibly postural tremor due to lesions affecting the cerebellothalamic and dopaminergic systems—such as involving the brainstem, cerebellum, and thalamus and, possibly, their pathways.

Palatal tremors. These rhythmic movements of the soft palate may or may not occur subsequent to lesions of the brainstem and cerebellum and associated olivary pseudohypertrophy.

Neuropathic tremor syndrome. Certain peripheral neuropathies, particularly dysgammaglobulinemic neuropathies, are commonly associated with tremor, primarily kinetic and postural tremor of the affected extremities.

Drug-induced and toxic tremor syndromes. Pharmacologic agents used to treat other medical conditions may induce tremor. Such medications may include theophylline, valproate, lithium, tricyclic antidepressants, neuroleptics, sympathomimetics, amphetamines, steroids, certain agents used to treat endocrine and metabolic disorders, or other miscellaneous agents. Toxic tremor, such as seen in manganese, arsenic, or mercury intoxication or poisoning, occurs in association with other neurologic symptoms, such as gait disturbances, rigidity, dystonia, ataxia, dysarthria, confusion, etc.

Psychogenic tremor. This form of tremor may be suggested by a history of somatization, the presence of unrelated neurologic signs, and sudden tremor onset or remissions.

Myorhythmia. A slow tremor of 2 to 4 Hz as seen in patients with lesions of the brainstem (similar to Holmes tremor).

The precise mechanism underlying ET remains unknown. No distinct CNS pathology or structural lesion has been determined. However, several pathophysiologic theories have been proposed that implicate a central source of tremorogenic oscillation. More specifically, ET is thought to arise from a central oscillatory activity within a central network or cell group that enters an oscillatory mode. In this model, interconnected oscillatory loops in the nervous system with oscillations in the olivo-cerebello-rubral loops release normal dampening influences and allow spinal reflex loop oscillations. It has also been proposed that stretch loop circuits as well as circuits within the CNS may become unstable and drive muscle contractions (central oscillators), or a combination of both stretch loop and CNS circuits, to produce tremor as in ET.

Peripheral factors may contribute to tremor as well. Beta-adrenergic blockers such as propranolol attenuate ET and physiologic tremor (PT), possibly via peripheral $beta_2$ adrenoreceptors. In addition, intravenous and intra-arterial epinephrine enhance physiologic tremor via peripheral forearm beta-adrenoreceptors, blocked by propranolol. However, beta-blockers may also affect central pathways.

Drug therapy may be a reasonable option for any ET patient with disabling tremor, since certain therapeutic agents may have a tremorolytic effect. Most patients benefit from pharmacologic therapy, with many experiencing a significant attenuation of tremor (see Table 3). However, only rarely does tremor recede completely. In addition, it is possible that tolerance may be reported by some patients who are undergoing long-term therapy, potentially signifying increasing tremor severity with time.

TABLE 3

Selected pharmacotherapeutic options for essential tremor

| Drug | Precautions and side effects | Comments |
|---|---|---|
| Beta blockers | Avoid in patients with asthma, bradycardia, heart failure, or diabetes (therapy masks signs of hypoglycemia); may cause significant memory loss and confusion in the elderly | Useful first-line drugs; best tolerated by younger patients |
| Propranolol HCl | | Most common first-line drug |
| Metoprolol | | Alternative to propranolol for first-line therapy |
| Anti-convulsants | | |
| Primidone | May cause flulike symptoms, ataxia, and drowsiness | Useful first-line drug; may be effective even in patients who are unresponsive to beta blockers |
| Gabapentin | May cause mild drowsiness, headache, and abdominal discomfort | Useful second-line drug; well-tolerated by the elderly |
| Benzodiazepines | May cause confusion, drowsiness, ataxia, hypotension, and apnea | Useful second-line drugs, particularly in anxiety-exacerbated tremors |
| Clonazepam | Same as above | Most common benzodiazepine prescribed for essential tremor |
| Diazepam | Same as above | |
| Calcium channel blockers e.g. nimodipine or nicardipine | May cause hypotension | May be an option if first- and second-line drugs fail |
| Carbonic anhydrase inhibitors | | May be an option if first- and second-line drugs fail |
| Methazolamide | May cause significant paresthesias, abdominal discomfort, and drowsiness | Side effects may limit usefulness; may be beneficial for voice and head tremors |
| Topiramate | May cause mild paresthesias, abdominal discomfort, and drowsiness | Anticonvulsant; better tolerated than methazolamide |

Varying degrees of control in ET have been obtained with these drugs. However, neither of these agents will benefit every patient. Generally, the first-line therapies are associated with side effects especially in elderly people suffering from comorbidities. Since the incidence of ET is increasing with age an effective and safe therapy is lacking.

The use of compounds of Formula (Ib) or/and Formula (IIb) for treatment of tremor has not been reported. Thus, the present invention concerns the use of said compounds of Formulae (Ib) or/and (IIb) for the preparation of a pharmaceutical composition for the prevention, alleviation or/and treatment of tremor such as, but not limited to, essential tremor, physiologic tremor, enhanced physiologic tremor, undetermined tremor syndrome, primary orthostatic tremor, dystonic tremor, task- and position-specific tremors, parkinsonian tremor syndromes, cerebellar tremor syndromes, Holmes tremor, palatal tremors, neuropathic tremor syndrome, drug-induced and toxic tremor syndromes, psychogenic tremor, myorhythmia, rest tremor, action tremor, postural tremor, kinetic tremor, task- or position-specific tremor or/and isometric tremor.

Surprisingly, the application of compounds (Ib) or/and (IIb), particularly (R)-2-acetamide-N-benzyl-3-methoxypropionamide (SPM 927) reduced the intensity and the total duration of harmaline-induced tremor in rats. Moreover, the latency of tremor onset following harmaline injection was markedly increased. These results indicate that SPM 927 is useful for the treatment of tremor.

A compound according to the invention has the general Formula (Ib)

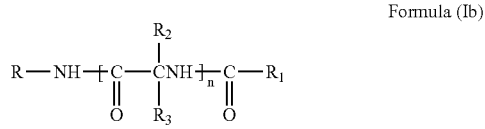

Formula (Ib)

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl or lower cycloalkyl lower alkyl, and R is unsubstituted or is substituted with at least one electron withdrawing group, and/or at least one electron donating group;

$R_1$ is hydrogen or lower alkyl, lower alkenyl, lower alkynyl, aryl lower alkyl, aryl, heterocyclic lower alkyl, lower alkyl heterocyclic, heterocyclic, lower cycloalkyl, lower cycloalkyl lower alkyl, each unsubstituted or substituted with at least one electron donating group and/or at least one electron withdrawing group;

and $R_2$ and $R_3$ are independently hydrogen, lower alkyl, lower alkenyl, lower alkynyl, aryl lower alkyl, aryl, halo, heterocyclic, heterocyclic lower alkyl, lower alkyl heterocyclic, lower cycloalkyl, lower cycloalkyl lower alkyl, or Z-Y wherein $R_2$ and $R_3$ may be unsubstituted or substituted with at least one electron withdrawing group and/or at least one electron donating group;

Z is O, S, S(O)$_a$, NR$_4$, NR'$_6$, PR$_4$ or a chemical bond;

Y is hydrogen, lower alkyl, aryl, aryl lower alkyl, lower alkenyl, lower alkynyl, halo, heterocyclic, heterocyclic lower alkyl, lower alkyl heterocyclic and Y may be unsubstituted or substituted with at least one electron donating group and/or at least one electron withdrawing group, provided that when Y is halo, Z is a chemical bond, or ZY taken together is NR$_4$NR$_5$R$_7$, NR$_4$OR$_5$, ONR$_4$R$_7$, OPR$_4$R$_5$, PR$_4$OR$_5$, SNR$_4$R$_7$, NR$_4$SR$_7$, SPR$_4$R$_5$, PR$_4$SR$_7$, NR$_4$P$_5$, PR$_4$NR$_5$R$_7$ or N$^+$R$_5$R$_6$R$_7$,

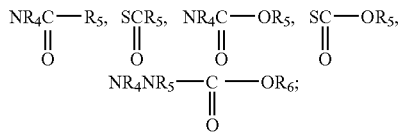

R'$_6$ is hydrogen, lower alkyl, lower alkenyl, or lower alkenyl which may be unsubstituted or substituted with at least one electron withdrawing group or/and at least one electron donating group;

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may independently be unsubstituted or substituted with at least one electron withdrawing group or/and at least one electron donating group;

$R_7$ is $R_6$ or COOR$_8$ or COR$_8$, which $R_7$ may be unsubstituted or substituted with at least one electron withdrawing group or/and at least one electron donating group;

$R_8$ is hydrogen or lower alkyl, or aryl lower alkyl, and the aryl or alkyl group may be unsubstituted or substituted with at least one electron withdrawing group or/and at least one electron donating group; and n is 1-4; and a is 1-3.

Preferably the compound according has the general Formula (IIb)

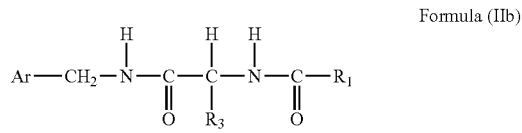

Formula (IIb)

wherein

Ar is aryl, especially phenyl, which is unsubstituted or substituted with at least one halo; $R_3$ is —CH$_2$-Q, wherein Q is lower alkoxy; and $R_1$ is lower alkyl, especially methyl.

The present invention is also directed to a pharmaceutical composition comprising a compound according to Formula (Ib) or/and Formula (IIb) useful for the prevention, alleviation or/and treatment of tremors such as, but not limited to, essential tremor, physiologic tremor, enhanced physiologic tremor, undetermined tremor syndrome, primary orthostatic tremor, dystonic tremor, task- and position-specific tremors, parkinsonian tremor syndromes, cerebellar tremor syndromes, Holmes tremor, palatal tremors, neuropathic tremor syndrome, drug-induced and toxic tremor syndromes, psychogenic tremor, myorhythmia, rest tremor, action tremor, postural tremor, kinetic tremor, task- or position-specific tremor or/and isometric tremor.

The "lower alkyl" groups when used alone or in combination with other groups, are lower alkyl containing from 1 to 6 carbon atoms, especially 1 to 3 carbon atoms, and may be straight chain or branched. These groups include methyl, ethyl, propyl, isopropyl, butyl, isobutyl, tertiary butyl, amyl, hexyl, and the like.

The "lower alkoxy" groups are lower alkoxy containing from 1 to 6 carbon atoms, especially 1 to 3 carbon atoms, and may be straight chain or branched. These groups include methoxy, ethoxy, propoxy, butoxy, isobutoxy, tert-butoxy, pentoxy, hexoxy and the like.

The "aryl lower alkyl" groups include, for example, benzyl, phenylethyl, phenylpropyl, phenylisopropyl, phenylbutyl, diphenylmethyl, 1,1-diphenylethyl, 1,2-diphenylethyl, and the like.

The term "aryl", when used alone or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polycyclic and are fused rings. A polynuclear aromatic compound as used herein, is meant to encompass bicyclic and tricyclic fused aromatic ring systems containing from 10-18 ring carbon atoms and up to a total of 25 carbon atoms. The aryl group includes phenyl, and the polynuclear aromatics e.g., naphthyl, anthracenyl, phenanthrenyl, azulenyl and the like. The aryl group also includes groups like ferrocenyl. Aryl groups may be unsubstituted or mono or polysubstituted with electron withdrawing or/and electron donating groups as described below.

"Lower alkenyl" is an alkenyl group containing from 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1,3 or 2,4-pentadienyl, and the like.

The term "lower alkynyl" is an alkynyl group containing 2 to 6 carbon atoms and may be straight chained as well as branched. It includes such groups as ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like.

The term "lower cycloalkyl" when used alone or in combination is a cycloalkyl group containing from 3 to 18 ring carbon atoms and up to a total of 25 carbon atoms. The cycloalkyl groups may be monocyclic, bicyclic, tricyclic, or polycyclic and the rings are fused. The cycloalkyl may be completely saturated or partially saturated. Examples include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. Cycloalkyl includes the cis or trans forms. Cycloalkyl groups may be unsubstituted or mono or polysubstituted with electron withdrawing or/and electron donating groups as described below. Furthermore, the substituents may either be in endo or exo positions in the bridged bicyclic systems.

The term "electron-withdrawing and electron donating" refer to the ability of a substituent to withdraw or donate electrons, respectively, relative to that of hydrogen if the hydrogen atom occupied the same position in the molecule. These terms are well understood by one skilled in the art and are discussed in Advanced Organic Chemistry, by J. March, John Wiley and Sons, New York, N.Y., pp.16-18 (1985) and the discussion therein is incorporated herein by reference. Electron withdrawing groups include halo, including bromo, fluoro, chloro, iodo and the like; nitro, carboxy, lower alkenyl, lower alkynyl, formyl, carboxyamido, aryl, quaternary ammonium, haloalkyl such as trifluoromethyl, aryl lower alkanoyl, carbalkoxy and the like. Electron donating groups include such groups as hydroxy, lower alkoxy, including methoxy, ethoxy and the like; lower alkyl, such as methyl, ethyl, and the like; amino, lower alkylamino, di(loweralkyl) amino, aryloxy such as phenoxy, mercapto, lower alkylthio, lower alkylmercapto, disulfide (lower alkyldithio) and the like. One of ordinary skill in the art will appreciate that some of the aforesaid substituents may be considered to be electron donating or electron withdrawing under different chemical conditions. Moreover, the present invention contemplates any combination of substituents selected from the above-identified groups.

The term "halo" includes fluoro, chloro, bromo, iodo and the like.

The term "acyl" includes lower alkanoyl containing from 1 to 6 carbon atoms and may be straight chains or branched. These groups include, for example, formyl, acetyl, propionyl, butyryl, isobutyryl, tertiary butyryl, pentanoyl and hexanoyl.

As employed herein, a heterocyclic group contains at least one sulfur, nitrogen or oxygen ring atom, but also may include several of said atoms in the ring. The heterocyclic groups contemplated by the present invention include heteroaromatics and saturated and partially saturated heterocyclic compounds. These heterocyclics may be monocyclic, bicyclic, tricyclic or polycyclic and are fused rings. They may preferably contain up to 18 ring atoms and up to a total of 17 ring carbon atoms and a total of up to 25 carbon atoms. The heterocyclics are also intended to include the so-called benzoheterocyclics. Representative heterocyclics include furyl, thienyl, pyrazolyl, pyrrolyl, methylpyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imadazolindinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the N-oxides of pyridyl, pyrazinyl, and pyrimidinyl and the like. Heterocyclic groups may be unsubstituted or mono or polysubstituted with electron withdrawing or/and electron donating groups.

The preferred heterocyclics are thienyl, furyl, pyrrolyl, benzofuryl, benzothienyl, indolyl, methylpyrrolyl, morpholinyl, pyridiyl, pyrazinyl, imidazolyl, pyrimidinyl, or pyridazinyl. The preferred heterocyclic is a 5 or 6-membered heterocyclic compound. The especially preferred heterocyclic is furyl, pyridyl, pyrazinyl, imidazolyl, pyrimidinyl, or pyridazinyl. The most preferred heterocyclics are furyl and pyridyl.

The preferred compounds are those wherein n is 1, but di (n=2), tri (n=3) and tetrapeptides (n=4) are also contemplated to be within the scope of the invention.

The preferred values of R is aryl lower alkyl, especially benzyl especially those wherein the phenyl ring thereof is unsubstituted or substituted with electron donating groups or/and electron withdrawing groups, such as halo (e.g., F).

The preferred $R_1$ is H or lower alkyl. The most preferred $R_1$ group is methyl.

The preferred electron donating substituents or/and electron withdrawing substituents are halo, nitro, alkanoyl, formyl, arylalkanoyl, aryloyl, carboxyl, carbalkoxy, carboxamido, cyano, sulfonyl, sulfoxide, heterocyclic, guanidine, quatemary ammonium, lower alkenyl, lower alkynyl, sulfonium salts, hydroxy, lower alkoxy, lower alkyl, amino, lower alkylamino, di(loweralkyl) amino, amino lower alkyl, mercapto, mercaptoalkyl, alkylthio, and alkyldithio. The term "sulfide" encompasses mercapto, mercapto alkyl and alkylthio, while the term disulfide encompasses alkyldithio. Especially preferred electron donating or/and electron withdrawing groups are halo or lower alkoxy, most preferred are fluoro or methoxy. These preferred substituents may be present on any one of the groups in Formula (Ib) or/and (IIb), e.g. R, $R_1$, $R_2$, $R_3$, $R_4$, $R_5$, $R_6$, $R'_6$, $R_7$, $R_8$ and/or $R_{50}$ as defined herein.

The ZY groups representative of $R_2$ and $R_3$ include hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; lower dialkylamino, such as, dimethylamino; trialkyl ammonium salt, hydrazino; alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), lower alkoxy amino [(NHOR$_{18}$) wherein R$_{18}$ is lower alkyl], N-lower alkylhydroxyl amino [(NR$_{18}$)OH wherein R$_{18}$ is lower alkyl], N-lower alkyl-O-lower alkylhydroxyamino, i.e., [N(R$_{18}$)OR$_{19}$ wherein R$_{18}$ and R$_{19}$ are independently lower alkyl], and o-hydroxylamino (—O—NH$_2$); alkylamido such as acetamido; trifluoroacetamido; lower alkoxyamino, (e.g., NH(OCH$_3$)); and heterocyclicamino, such as pyrazoylamino.

The preferred heterocyclic groups representative of R$_2$ and R$_3$ are monocyclic 5- or 6-membered heterocyclic moieties of the formula:

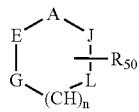

or those corresponding partially or fully saturated form thereof wherein n is 0 or 1; and
R$_{50}$ is H or an electron withdrawing group or electron donating group;
A, E, L, J and G are independently CH, or a heteroatom selected from the group consisting of N, O, S;

but when n is 0, G is CH, or a heteroatom selected from the group consisting of NH, O and S with the proviso that at most two of A, E, L, J and G are heteroatoms.

When n is 0, the above heteroaromatic moiety is a five membered ring, while if n is 1, the heterocyclic moiety is a six membered monocyclic heterocyclic moiety. The preferred heterocyclic moieties are those aforementioned heterocyclics which are monocyclic.

If the ring depicted hereinabove contains a nitrogen ring atom, then the N-oxide forms are also contemplated to be within the scope of the invention.

When R$_2$ or R$_3$ is a heterocyclic of the above formula, it may be bonded to the main chain by a ring carbon atom. When n is 0, R$_2$ or R$_3$ may additionally be bonded to the main chain by a nitrogen ring atom.

Other preferred moieties of R$_2$ and R$_3$ are hydrogen, aryl, e.g., phenyl, aryl alkyl, e.g., benzyl and alkyl.

It is to be understood that the preferred groups of R$_2$ and R$_3$ may be unsubstituted or mono or poly substituted with electron donating or/and electron withdrawing groups. It is preferred that R$_2$ and R$_3$ are independently hydrogen, lower alkyl, which is either unsubstituted or substituted with electron withdrawing groups or/and electron donating groups, such as lower alkoxy (e.g., methoxy, ethoxy, and the like), N-hydroxyamino, N-lower alkylhydroxyamino, N-loweralkyl-O-loweralkyl and alkylhydroxyamino.

It is preferred that one of R$_2$ and R$_3$ is hydrogen.
It is preferred that n is one.
It is more prefered that n=1 and one of R$_2$ and R$_3$ is hydrogen. It is especially preferred that in this embodiment, R$_2$ is hydrogen and R$_3$ is lower alkyl or ZY; Z is O, NR$_4$ or PR$_4$; Y is hydrogen or lower alkyl; ZY is NR$_4$NR$_5$R$_7$, NR$_4$OR$_5$, ONR$_4$R$_7$,

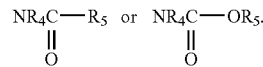

In another especially preferred embodiment, n=1, R$_2$ is hydrogen and R$_3$ is lower alkyl which may be substituted or unsubstituted with an electron donating or electron withdrawing group, NR$_4$OR$_5$, or ONR$_4$R$_7$, In yet another especially preferred embodiment, n=1, R$_2$ is hydrogen and R$_3$ is lower alkyl which is unsubstituted or substituted with hydroxy or loweralkoxy, NR$_4$OR$_5$ or ONR$_4$R$_7$, wherein R$_4$, R$_5$ and R$_7$ are independently hydrogen or lower alkyl, R is aryl lower alkyl, which aryl group may be unsubstituted or substituted with an electron withdrawing group and R$_1$ is lower alkyl. In this embodiment it is most preferred that aryl is phenyl, which is unsubstituted or substituted with halo.

It is preferred that R$_2$ is hydrogen and R$_3$ is hydrogen, an alkyl group which is unsubstituted or substituted by at least an electron donating or electron withdrawing group or ZY. In this preferred embodiment, it is more preferred that R$_3$ is hydrogen, an alkyl group such as methyl, which is unsubstituted or substituted by an electron donating group, or NR$_4$OR$_5$ or ONR$_4$R$_7$, wherein R$_4$, R$_5$ and R$_7$ are independently hydrogen or lower alkyl. It is preferred that the electron donating group is lower alkoxy, and especially methoxy or ethoxy.

It is preferred that R$_2$ and R$_3$ are independently hydrogen, lower alkyl, or ZY;
Z is O, NR$_4$ or PR$_4$;
Y is hydrogen or lower alkyl or
ZY is NR$_4$R$_5$R$_7$, NR$_4$OR$_5$, ONR$_4$R$_7$,

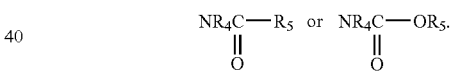

It is also preferred that R is aryl lower alkyl. The most preferred aryl for R is phenyl. The most preferred R group is benzyl. In a preferred embodiment, the aryl group may be unsubstituted or substituted with an electron donating or electron withdrawing group. If the aryl ring in R is substituted, it is most preferred that it is substituted with an electron withdrawing group, especially on the aryl ring. The most preferred electron withdrawing group for R is halo, especially fluoro.

The preferred R$_1$ is lower alkyl, especially methyl.

It is more preferred that R is aryl lower alkyl and R$_1$ is lower alkyl.

Further preferred compounds are compounds of Formula (Ib) wherein n is 1; R$_2$ is hydrogen; R$_3$ is hydrogen, a lower alkyl group, especially methyl which is substituted by an electron donating or electron withdrawing group or ZY; R is aryl, aryl lower alkyl, such as benzyl, wherein the aryl group is unsubstituted or substituted with an electron donating or electron withdrawing group and R$_1$ is lower alkyl. In this embodiment, it is more preferred that R$_3$ is hydrogen, a lower alkyl group, especially methyl, which may be substituted by electron donating group, such as lower alkoxy, (e.g., methoxy, ethoxy and the like), NR$_4$OR$_5$ or ONR$_4$R$_7$ wherein these groups are defined hereinabove.

The most preferred compounds utilized are those of the Formula (IIb):

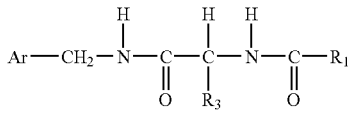

Formula (IIb)

wherein
Ar is aryl, especially phenyl, which is unsubstituted or substituted with at least one electron donating group or electron withdrawing group, especially halo,
$R_1$ is lower alkyl, especially containing 1-3 carbon atoms; and
$R_3$ is as defined herein, but especially hydrogen, loweralkyl, which is unsubstituted or substituted by at least an electron donating group or electron withdrawing group or ZY. It is even more preferred that $R_3$ is, in this embodiment, hydrogen, an alkyl group which is unsubstituted or substituted by an electron donating group, $NR_4OR_5$ or $ONR_4R_7$. It is most preferred that $R_3$ is $CH_2$-Q, wherein Q is lower alkoxy, especially containing 1-3 carbon atoms; $NR_4OR_5$ or $ONR_4R_7$ wherein $R_4$ is hydrogen or alkyl containing 1-3 carbon atoms, $R_5$ is hydrogen or alkyl containing 1-3 carbon atoms, and $R_7$ is hydrogen or alkyl containing 1-3 carbon atoms.

The most preferred $R_1$ is $CH_3$. The most preferred R3 is $CH_2$-Q, wherein Q is methoxy.

The most preferred aryl is phenyl. The most preferred halo is fluoro.

The most preferred compounds include:
(R)-2-acetamido-N-benzyl-3-methoxy-propionamide;
O-methyl-N-acetyl-D-serine-m-fluorobenzyl-amide;
O-methyl-N-acetyl-D-serine-p-fluorobenzyl-amide;
N-acetyl-D-phenylglycine benzylamide;
D-1,2-(N,O-dimethylhydroxylamino)-2-acetamide acetic acid benzylamide;
D-1,2-(O-methylhydroxylamino)-2-acetamido acetic acid benzylamide.

It is to be understood that the various combinations and permutations of the Markush groups of $R_1$, $R_2$, $R_3$, R and n described herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$, and R with respect to each value of n.

The compounds utilized in the present invention may contain one or more asymmetric carbons and may exist in racemic and optically active forms. The configuration around each asymmetric carbon can be either the D or L form. It is well known in the art that the configuration around a chiral carbon atoms can also be described as R or S in the Cahn-Prelog-Ingold nomenclature system. All of the various configurations around each asymmetric carbon, including the various enantiomers and diastereomers as well as racemic mixtures and mixtures of enantiomers, diastereomers or both are contemplated by the present invention.

In the principal chain, there exists asymmetry at the carbon atom to which the groups $R_2$ and $R_3$ are attached. When n is 1, the compounds of the present invention is of the formula

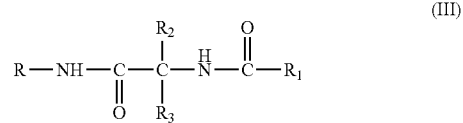

(III)

wherein R, $R_1$, $R_2$, $R_3$, $R_4$, $R_5$, $R_6$, $R'_6$, $R_7$, $R_8$, $R_{50}$, Z and Y are as defined previously.

As used herein, the term configuration shall refer to the configuration around the carbon atom to which $R_2$ and $R_3$ are attached, even though other chiral centers may be present in the molecule. Therefore, when referring to a particular configuration, such as D or L, it is to be understood to mean the D or L stereoisomer at the carbon atom to which $R_2$ and $R_3$ are attached. However, it also includes all possible enantiomers and diastereomers at other chiral centers, if any, present in the compound.

The compounds of the present invention are directed to all the optical isomers, i.e., the compounds of the present invention are either the L-stereoisomer or the D-stereoisomer (at the carbon atom to which $R_2$ and $R_3$ are attached). These stereoisomers may be found in mixtures of the L and D stereoisomer, e.g., racemic mixtures. The D stereoisomer is preferred.

More preferred is a compound of Formula (III) in the R configuration, preferably substantially enantiopure, wherein the substituent R is benzyl which is unsubstituted or substituted with at least one halo group, wherein $R_3$ is $CH_2$-Q, wherein Q is lower alkoxy containing 1-3 carbon atoms and wherein $R_1$ is methyl. Preferably R is unsubstituted benzyl or benzyl substituted with at least one halo group which is a fluoro group.

Depending upon the substituents, the present compounds may form addition salts as well. All of these forms are contemplated to be within the scope of this invention including mixtures of the stereoisomeric forms.

The manufacture of the utilized compounds is described in U.S. Pat. Nos. 5,378,729 and 5,773,475, the contents of both of which are incorporated by reference.

The compounds utilized in the present invention are useful as such as depicted in the Formulae (Ib) or/and (IIb) or can be employed in the form of salts in view of its basic nature by the presence of the free amino group. Thus, the compounds of Formulae (Ib) or/and (IIb) form salts with a wide variety of acids, inorganic and organic, including pharmaceutically acceptable acids. The salts with therapeutically acceptable acids are of course useful in the preparation of formulation where enhanced water solubility is most advantageous.

These pharmaceutically acceptable salts have also therapeutic efficacy. These salts include salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, perchloric, glycolic, gluconic, succinic, aryl sulfonic, (e.g., p-toluene sulfonic acids, benzenesulfonic), phosphoric, malonic, and the like.

The present invention is further directed to a method for the prevention, alleviation or/and treatment of a disease or condition as described above in a mammal, including a human being, comprising administering at least one compound of Formulae (Ib) or/and (IIb).

It is preferred that the compound utilized in the present invention is used in therapeutically effective amounts.

The physician will determine the dosage of the present therapeutic agents which will be most suitable and it will vary with the form of administration and the particular compound chosen, and furthermore, it will vary with the patient under treatment, the age of the patient, the type of malady being treated. He will generally wish to initiate treatment with small dosages substantially less than the optimum dose of the compound and increase the dosage by small increments until the optimum effect under the circumstances is reached. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

In a preferred embodiment, the compounds of the present invention are administered in amounts ranging from about 1 mg to about 100 mg per kilogram of body weight per day, preferably in amounts ranging from about 1 mg to about 10 mg per kilogram of body weight per day. This dosage regimen may be adjusted by the physician to provide the optimum therapeutic response. Patients in need thereof may be treated with doses of the compound of the present invention of at least 50 mg/day, preferably of at least 200 mg/day, more preferably of at least 300 mg/day and most preferably of at least 400 mg/day. Generally, a patient in need thereof may be treated with doses at a maximum of 6 g/day, more preferably a maximum of 1 g/day and most preferably a maximum of 600 mg/day. In some cases, however, higher or lower doses may be needed.

In another preferred embodiment, the daily doses are increased until a predetermined daily dose is reached which is maintained during the further treatment.

In yet another preferred embodiment, several divided doses may be administered daily. For example, three doses per day may be administered, preferably two doses per day. It is more preferred to administer a single dose per day.

In yet another preferred embodiment, an amount of the compounds of the present invention may be administered which results in a plasma concentration of 0.1 to 15 µg/ml (trough) and 5 to 18.5 µg/ml (peak), calculated as an average over a plurality of treated subjects.

The compounds of Formulae (Ib) or/and (IIb) may be administered in a convenient manner, such as by oral, intravenous (where water soluble), intramuscular, intrathecal or subcutaneous routes. Oral or/and i.v. administration is preferred.

The pharmaceutical composition of the present invention may be prepared for the treatment regimen as described above, in particular for the treatment with doses as described above, to effect plasma concentrations as described above, for administration periods or/and administration routes as specified in the embodiments of the present invention as described above.

In another preferred embodiment, the method of the present invention as described above for the treatment of a mammal including a human being in need thereof comprises administering a compound of the present invention in combination with administering a further active agent for the prevention, alleviation or/and treatment of tremor. The compound of the present invention and the further active agent may be administered together, i.e. in a single dose form, or may be administered separately, i.e. in a separate dose form. Thus, the pharmaceutical composition of the present invention may comprise a compound of the present invention as defined above and may further comprise a further active agent for the prevention, alleviation or/and treatment of tremor. The pharmaceutical composition may comprise a single dose form or may comprise a separate dose form comprising a first composition comprising a compound of the present invention as defined above and a second composition comprising the further active agent.

The compounds of the present invention may be used for the preparation of a pharmaceutical composition as described above.

The compounds of Formulae (Ib) or/and (IIb) may be orally administered, for example, with an inert diluent or with an assimilable edible carrier, or it may be enclosed in hard or soft shell gelatin capsules, or it may be compressed into tablets, or it may be incorporated directly into the fool of the diet. For oral therapeutic administration, the active compound of Formulae (Ib) or/and (IIb) may be incorporated with excipients and used in the form of ingestible tablets, buccal tablets, troches, capsules, elixirs, suspensions, syrups, wafers, and the like. Such compositions and preparations should contain at least 1% of active compound of Formulae (Ib) or/and (IIb). The percentage of the compositions and preparations may, of course, be varied and may conveniently be between about 5 to about 80% of the weight of the unit. The amount of active compound of Formulae (Ib) or/and (IIb) in such therapeutically useful compositions is such that a suitable dosage will be obtained. Preferred compositions or preparations according to the present invention contains between about 10 mg and 6 g active compound of Formulae (Ib) or/and (IIb).

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid, polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying the freeze-drying technique plus any additional desired ingredient from previously sterile-filtered solution thereof.

As used herein, "pharmaceutically acceptable carrier" includes any and all solvents, dispersion media, coatings, antibacterial and antifungal agent, isotonic and absorption delaying agents for pharmaceutical active substances as well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form or ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material an the particular therapeutic effect to be achieved, and (b) the limitations inherent in the art of compounding such as active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 10 mg to about 6 g. Expressed in proportions, the active compound is generally present in from about 1 to about 750 mg/ml of carrier. In the case of compositions containing supplementary active ingredients, the dosages are determined by reference to the usual dose and manner of administration of the said ingredients.

As used herein the term "patient" or "subject" refers to a warm blooded animal, and preferably mammals, such as, for example, cats, dogs, horses, cows, pigs, mice, rats and primates, including humans. The preferred patient is a human.

The term "treat" refers to either relieving the pain associated with a disease or condition, to curing or alleviating the patient's disease or condition.

The compounds of the present invention are administered to a patient suffering from the aforementioned type of disorder in an effective amount. These amounts are equivalent to the therapeutically effective amounts described hereinabove.

The following example shows the properties of SPM 927 in reducing harmaline-induced tremor in rats.

The used substance was SPM 927 which is the synonym for Harkoseride. The standard chemical nomenclature is (R)-2-acetamide-N-benzyl-3-methoxypropionamide. The international non-proprietary name of SPM 927 is lacosamide.

EXAMPLE

Effect of SPM 927 on Harmaline-induced Tremors in Rats

Objectives

The objective of the present study was to show that SPM 927 reduces harmaline-induced tremors in rats.

Methods Outline

1. Animals

Male Sprague-Dawley rats (Charles River Laboratories, France) were used. During the acclimatization period, animals were housed 2 per cage, in Makrolon type III cages, in the animal room (temperature: 20±2° C., humidity: minimum 45%, air changes: >12 per hour, light/dark cycle of 12 h/12 h [on at 7:00 A.M.]). Animals were allowed a minimum of 5 days period before experiment for acclimatization.

Animals received certified food (Provimi-Kliba Nafag, Switzerland, ref. 3433) and water (tap water in water bottle) ad libitum. Water is analysed once a month for chemical contaminants and at least every three months for bacterial contaminants. Rats were placed on certified sawdust bedding in their cages (Goldchips Litalabo, ref. 891022, Trouw Nutrition France, Vigny, France).

2. Administration

Harmaline HCl (Sigma) was diluted in saline and injected at 20 mg/kg, i.p. The reference compound, propanolol was injected i.p. at 20 mg/kg, 30 min before harmaline administration. SPM 927 was given i.p. at 3, 10 and 30 mg/kg, 30 min before harmaline administration.

3. Harmaline-induced Tremors

The following parameters were assessed by an observer blind to the treatment of the animals.

Intensity: from 0 to 4 (0: no tremor, 1: mild tremor, 2: moderate intermittent tremor, 3: moderate persistent tremor, 4: pronounced severe tremor). Intensity will be scored every 30 min and for a total period of 120 min after harmaline administration.

Latency of onset

Total duration of tremor (max observation time: 120 min)

% rat displaying tremor

Results

TABLE 1

Effects of SPM 927 on harmaline-induced tremor intensity

| Treatment | Intensity of tremors after harmaline administration (score) | | | |
| --- | --- | --- | --- | --- |
| | +30 min Mean ± S.E.M. | +60 min Mean ± S.E.M. | +90 min Mean ± S.E.M. | +120 min Mean ± S.E.M. |
| Control | 0.0 ± 0.0 | 0.0 ± 0.0 | 0.0 ± 0.0 | 0.0 ± 0.0 |
| Vehicle, 2 mL/kg | 2.8 ± 0.1 ✓✓✓ | 3.0 ± 0.3 ✓✓✓ | 2.8 ± 0.2 ✓✓✓ | 2.9 ± 0.3 ✓✓✓ |
| Propranolol, 20 mg/kg | 1.6 ± 0.2** | 2.3 ± 0.3* | 1.6 ± 0.3* | 1.4 ± 0.3** |
| SPM 927, 3 mg/kg | 2.0 ± 0.4* | 2.0 ± 0.3* | 2.1 ± 0.4 | 1.8 ± 0.4* |
| SPM 927, 10 mg/kg | 2.0 ± 0.2** | 1.1 ± 0.3*** | 2.2 ± 0.4 | 1.3 ± 0.3** |
| SPM 927, 30 mg/kg | 0.9 ± 0.4** | 1.1 ± 0.3** | 1.4 ± 0.3** | 1.2 ± 0.2** |

✓✓✓ $p < 0.001$ versus the negative control group.
*$p < 0.05$,
**$p < 0.01$,
***$p < 0.001$ versus the vehicle group.

The Table 1 shows that harmaline administration induced tremors were vigorous for a moment but suddenly disappeared and sporadically reappeared. Tremors were still present at the end of the observation, 120 min post-harmaline administration.

SPM 927, given at 3, 10 and 30 mg/kg, reduced the intensity of harmaline-induced tremors in a dose dependent manner. At the highest dose tested, this effect was statistically significant at each test time-point (p<0.01 versus harmaline-treated group) and the maximal efficacy was higher than that of the positive reference compound propranolol. Administration of the reference compound propranolol at 20 mg/kg (the most efficacious dose based on literature data) reduced the intensity of tremors in a statistically significant manner at each time-point of observation.

Since harmaline-induced tremors are regarded a valid animal model for essential tremor these results indicate that SPM 927 is useful for the treatment of essential tremor. Moreover, due to the overlapping pathophysiologies of the different tremors, SPM 927 is indicated for the treatment of other tremors such as, but not limited to, physiologic tremor, enhanced physiologic tremor, undetermined tremor syndrome, primary orthostatic tremor, dystonic tremor, task- and position-specific tremors, parkinsonian tremor syndromes, cerebellar tremor syndromes, Holmes tremor, palatal tremors, neuropathic tremor syndrome, drug-induced and toxic tremor syndromes, psychogenic tremor or/and myorhythmia.

The invention claimed is:

1. A method for treating tremor in a subject in need thereof, the method comprising administering to the subject the compound (R)-2-acetamido-N-benzyl-3-methoxypropionamide or a pharmaceutically acceptable salt thereof, wherein the tremor comprises rhythmic oscillatory movement.

2. The method of claim 1, wherein the tremor is selected from the group consisting of essential tremor, physiologic tremor, enhanced physiologic tremor, undetermined tremor syndrome, primary orthostatic tremor, dystonic tremor, task- and position-specific tremors, parkinsonian tremor syndromes, cerebellar tremor syndromes, Holmes's tremor, palatal tremors, neuropathic tremor syndrome, drug-induced and toxic tremor syndromes, psychogenic tremor, myorhythmia, rest tremor, action tremor, postural tremor, kinetic tremor, isometric tremor and combinations thereof.

3. The method of claim 1, wherein the compound is administered in a pharmaceutical composition at a dose of the compound of at least 100 mg/day.

4. The method of claim 1, wherein the compound is administered in a pharmaceutical composition at a dose of the compound not greater than 6 g/day.

5. The method of claim 1, wherein the compound is administered in a pharmaceutical composition at increasing daily doses until a predetermined daily dose is reached which is maintained during further treatment.

6. The method of claim 1, wherein the compound is administered in a pharmaceutical composition in no more than three doses per day.

7. The method of claim 1, wherein the compound is administered in a pharmaceutical composition resulting in a plasma concentration of the compound of 0.1 to 15 μg/ml (trough) and 5 to 18.5 μg/ml (peak), calculated as an average over a plurality of treated subjects.

8. The method of claim 1, wherein the compound is administered orally or intravenously in a pharmaceutical composition.

9. The method of claim 1, further comprising administering to the subject a further active agent for the treatment of tremor.

10. The method of claim 9, wherein the (R)-2-acetamido-N-benzyl-3-methoxypropionamide or salt thereof and the further active agent are administered in a single dose form or separate dose forms comprising a first composition comprising the (R)-2-acetamido-N-benzyl-3-methoxypropionamide or salt thereof and a second composition comprising the further active agent.

11. The method of claim 1 wherein the subject is a mammal.

12. The method of claim 11 wherein the subject is a human.

13. A pharmaceutical composition comprising
    (a) (R)-2-acetamido-N-benzyl-3-methoxypropionamide or a pharmaceutically acceptable salt thereof, and
    (b) a further active agent for the treatment of tremor.

14. The pharmaceutical composition according to claim 13 which is a single dose form or comprises separate dose forms comprising a first composition comprising the compound (a), and a second composition comprising the further active agent (b).

* * * * *